United States Patent
Takenouchi

(10) Patent No.: US 12,131,513 B2
(45) Date of Patent: Oct. 29, 2024

(54) MEDICAL IMAGE PROCESSING APPARATUS AND MEDICAL IMAGE PROCESSING METHOD FOR UTILIZING A CLASSIFICATION RESULT RELATING TO A MEDICAL IMAGE

(71) Applicant: FUJIFILM Corporation, Tokyo (JP)

(72) Inventor: Seiya Takenouchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 537 days.

(21) Appl. No.: 17/392,875

(22) Filed: Aug. 3, 2021

(65) Prior Publication Data

US 2021/0366593 A1 Nov. 25, 2021

Related U.S. Application Data

(63) Continuation of application No. PCT/JP2020/008729, filed on Mar. 2, 2020.

(30) Foreign Application Priority Data

Mar. 8, 2019 (JP) ................................ 2019-042742

(51) Int. Cl.
*G06V 10/25* (2022.01)
*G06F 18/2431* (2023.01)
(Continued)

(52) U.S. Cl.
CPC .......... *G06V 10/25* (2022.01); *G06F 18/2431* (2023.01); *G06T 7/0012* (2013.01);
(Continued)

(58) Field of Classification Search
CPC ...... G06V 10/25; G06V 10/454; G06V 10/82; G06V 2201/03; G16H 30/20; G16H 30/40;
(Continued)

(56) References Cited

U.S. PATENT DOCUMENTS 9,186,041 B2 * 11/2015 Kasumi ................ A61B 8/0841
2002/0099273 A1   7/2002 Bocionek et al.
(Continued)

FOREIGN PATENT DOCUMENTS

CN    102893306 A    1/2013
CN    103476329 A    12/2013
(Continued)

OTHER PUBLICATIONS

International Search Report issued in PCT/JP2020/008729; mailed Apr. 21, 2020.
(Continued)

*Primary Examiner* — Gabriel I Garcia

(74) *Attorney, Agent, or Firm* — Studebaker & Brackett PC

(57) ABSTRACT

The medical image processing apparatus includes: an image acquiring unit that acquires a medical image; a classification unit that classifies, on the basis of the medical image acquired by the image acquiring unit, the medical image or a region of interest included in the medical image; a notification information generating unit that generates, in accordance with a classification result of the classification, first notification information for display and second notification information for storage, the second notification information differing from the first notification information; and a storage that stores the medical image and the second notification information.

14 Claims, 11 Drawing Sheets

(51) Int. Cl.
  G06T 7/00      (2017.01)
  G06T 11/00     (2006.01)
  G06V 10/44     (2022.01)
  G06V 10/82     (2022.01)
  G09G 5/373     (2006.01)
  G16H 30/20     (2018.01)
  G16H 30/40     (2018.01)
  G16H 50/20     (2018.01)

(52) U.S. Cl.
  CPC ............ G06T 11/00 (2013.01); G06V 10/454 (2022.01); G06V 10/82 (2022.01); G09G 5/373 (2013.01); G16H 30/20 (2018.01); G16H 30/40 (2018.01); G16H 50/20 (2018.01); *G06T 2207/10068* (2013.01); *G06T 2207/30096* (2013.01); *G06V 2201/03* (2022.01); *G09G 2380/08* (2013.01)

(58) Field of Classification Search
  CPC ... G16H 50/20; G06F 18/2431; G06T 7/0012; G06T 11/00; G06T 2207/10068; G06T 2207/300096; G09G 5/373; G09G 2380/08
  USPC .......................................................... 382/128
  See application file for complete search history.

(56) References Cited

U.S. PATENT DOCUMENTS

| | | | | |
|---|---|---|---|---|
| 2006/0274928 | A1* | 12/2006 | Collins | G16H 30/40 382/132 |
| 2013/0342668 | A1 | 12/2013 | Kasumi et al. | |
| 2014/0055452 | A1 | 2/2014 | Hamada | |
| 2020/0258224 | A1* | 8/2020 | Endo | A61B 1/0005 |
| 2021/0183055 | A1* | 6/2021 | Rao | G06T 7/0012 |
| 2022/0399100 | A1* | 12/2022 | Iwai | G06T 7/0012 |

FOREIGN PATENT DOCUMENTS

| | | |
|---|---|---|
| JP | 2002-312472 A | 10/2002 |
| JP | 2013-103023 A | 5/2013 |
| JP | 2017-213058 A | 12/2017 |

OTHER PUBLICATIONS

International Preliminary Report on Patentability and Written Opinion issued in PCT/JP2020/008729; issued Aug. 25, 2021.

Michael F. Byrne et al.; "Real-time differentiation of adenomatous and hyperplastic diminutive colorectal polyps during analysis of unaltered videos of standard colonoscopy using a deep learning model," Gut Microbiota; vol. 68, No. 1; Jan. 1, 2019; pp. 94-100.

Chen Peng-Jen et al.; "Accurate Classification of Diminutive Colorectal Polyps Using Computer-Aided Analysis," Gastroenterology; vol. 154, No. 3; Oct. 16, 2017; pp. 568-575; Elsevier Inc. US.

Anonymous; "Internationalization and localization," Wikipedia; Sep. 10, 2016; total 7 pages; URL: http://web.archive.org/web/20160910175747/https://en.wikipedia.org/wiki/Internationalization_and_localization.

The extended European search report issued by the European Patent Office on Mar. 24, 2022, which corresponds to European Patent Application No. 20770998.1-1126 and is related to U.S. Appl. No. 17/392,875.

An Office Action mailed by China National Intellectual Property Administration on Sep. 1, 2023, which corresponds to Chinese Patent Application No. 202080015012.5 and is related to U.S. Appl. No. 17/392,875; with English language translation.

* cited by examiner

FIG. 4
| CLASSIFICATION RESULT | FOR DISPLAY | FOR STORAGE |
|---|---|---|
| NONNEOPLASTIC | NN | nonneoplastic |
| NEOPLASTIC | N | neoplastic |
| OTHER | O | other |
FIG. 5A
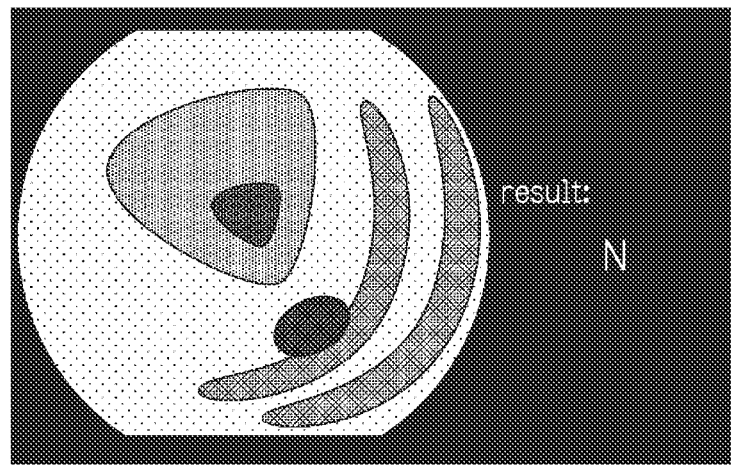
FIG. 5B
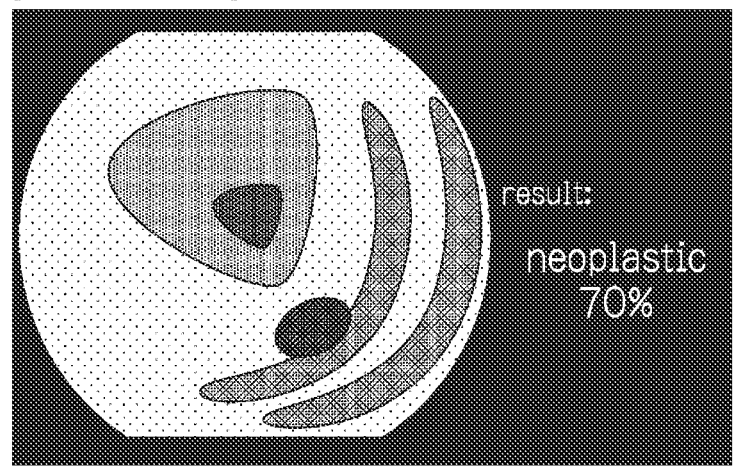

FIG. 9

| CLASSIFICATION RESULT | FOR DISPLAY 1 | FOR DISPLAY 2 | FOR STORAGE 1 | FOR STORAGE 2 |
|---|---|---|---|---|
| 1 | H | Type A | Hyperplastic | NICE Classification Type 1 |
| 2 | A | Type B | Adenoma | NICE Classification Type 2 |
| 3 | M | Type C | Malignancy | NICE Classification Type 3 |
| 4 | A | Adenoma | Adenoma | Adenoma 70% |

MEDICAL IMAGE PROCESSING APPARATUS AND MEDICAL IMAGE PROCESSING METHOD FOR UTILIZING A CLASSIFICATION RESULT RELATING TO A MEDICAL IMAGE

CROSS-REFERENCE TO RELATED APPLICATIONS

The present application is a Continuation of PCT International Application No. PCT/JP2020/008729 filed on Mar. 2, 2020 claiming priority under 35 U.S.C § 119(a) to Japanese Patent Application No. 2019-042742 filed on Mar. 8, 2019. Each of the above applications is hereby expressly incorporated by reference, in its entirety, into the present application.

BACKGROUND OF THE INVENTION

1. Field of the Invention

The present invention relates to a medical image processing apparatus and a medical image processing method, and particularly to a technique of notifying a physician and a patient of a classification result of automatically classifying a lesion or the like on the basis of a medical image.

2. Description of the Related Art

JP2017-213058A describes an image processing apparatus that makes a classification result to be provided to physicians and a classification result to be provided to patients differ from each other.

The image processing apparatus described in JP2017-213058A classifies, for each image included in a group of images captured in a time-series manner, a candidate lesion region in the image on the basis of a different standard (the degree of reliability as a candidate lesion). In addition, the image processing apparatus generates and outputs a first video signal to a first display apparatus for physicians and generates and outputs a second video signal to a second display apparatus for patients. By the first video signal, a candidate lesion region that is higher than or equal to a low-reliability standard and other regions can be distinguished from each other. By the second video signal, a candidate lesion region that is higher than or equal to a high-reliability standard and other regions can be distinguished from each other.

Thus, information that is not necessarily provided to patients (information of a low-reliability candidate lesion region) is not provided to patients so as not to make them feel anxious unnecessarily.

SUMMARY OF THE INVENTION

A support system that classifies whether a lesion is cancerous or non-cancerous on the basis of a medical image and that notifies a user of the classification result has been expected.

The notification of the classification result is desirably made by using words, a form, a position, and the like that do not hinder the user's diagnosis. In addition, if the notification is made in a manner by which it is clearly recognizable that the lesion is cancerous, a person other than the user, especially a patient, is made to feel anxious unnecessarily. However, a manner that is recognizable only by the user who performs examination may make it difficult to obtain understanding of experts at a conference or the like.

The image processing apparatus described in JP2017-213058A classifies a candidate lesion region in an image on the basis of a different reliability standard, generates a first video signal for physicians and a second video signal for patients, by which the classification result can be visualized, and causes a first display apparatus for physicians and a second display apparatus for patients to display the first video signal and the second video signal, respectively. Thus, it is not assumed that physicians and patients are notified of the same information (the same medical image and classification result). In addition, JP2017-213058A does not describe a storage that stores the medical image and the classification result in association with each other.

The present invention has been made in view of such circumstances, and an object thereof is to provide a medical image processing apparatus and a medical image processing method that generate notification information in a plurality of forms for display and for storage in accordance with a classification result of a medical image so as not to hinder examinations using the medical image and to sufficiently utilize a result for support based on the notification information.

In order to achieve the above object, a medical image processing apparatus according to an aspect of the present invention includes: an image acquiring unit that acquires a medical image; a classification unit that classifies, on the basis of the medical image acquired by the image acquiring unit, the medical image or a region of interest included in the medical image; a notification information generating unit that generates, in accordance with a classification result of the classification, first notification information for display and second notification information for storage, the second notification information differing from the first notification information; and a storage that stores the medical image and the second notification information.

According to the aspect of the present invention, on the basis of the acquired medical image, the medical image or the region of interest included in the medical image is classified, and, in accordance with the classification result of the classification, the first notification information for display and the second notification information for storage, the second notification information differing from the first notification information are generated. The generated second notification information for storage is stored in the storage together with the medical image. Here, by making the first notification information for display and the second notification information for storage differ from each other, the first notification information for display can be made first notification information in a notification form that is recognizable only by a user (physician) (form that is unrecognizable by a patient and the like), whereas the second notification information for storage can have a notification form that is understandable also by a person other than the user.

In a medical image processing apparatus according to another aspect of the present invention, the storage preferably stores a composite image in which the medical image and the second notification information are composited.

In a medical image processing apparatus according to a still another aspect of the present invention, the storage preferably stores the medical image and the second notification information in association with each other.

In a medical image processing apparatus according to a still another aspect of the present invention, the storage is preferably constituted by a plurality of storages, the notification information generating unit preferably generates a plurality of types of the second notification information whose upper limit equals to a total number of the plurality of storages, and each of the plurality of storages preferably stores the medical image and the second notification information corresponding to the storage, among the plurality of types of the second notification information.

A medical image processing apparatus according to a still another aspect of the present invention preferably further includes a display control unit that causes a display unit to display the medical image and the first notification information.

In a medical image processing apparatus according to a still another aspect of the present invention, the display unit is preferably constituted by a plurality of display units, the notification information generating unit preferably generates a plurality of types of the first notification information whose upper limit equals to a total number of the plurality of display units, and the display control unit preferably causes the plurality of display units to display the medical image and the plurality of types of the first notification information in a corresponding manner. For example, first notification information to be displayed on a display unit for a user may be made to differ from first notification information to be displayed on a display unit for a patient.

In a medical image processing apparatus according to a still another aspect of the present invention, the notification information generating unit preferably generates the first notification information in a notification form by which a patient does not understand details of the classification result and the second notification information indicating the details of the classification result.

In a medical image processing apparatus according to a still another aspect of the present invention, the classification result preferably includes information on a degree of reliability of a lesion classified by the classification unit, and the notification information generating unit preferably generates the first notification information in which the information on the degree of reliability is omitted and the second notification information including the information on the degree of reliability.

In a medical image processing apparatus according to a still another aspect of the present invention, the notification information generating unit preferably acquires a display region of the classification result on the basis of resolution information of a display unit and preferably generates the first notification information in which details of the classification result are simplified in accordance with a size of the display region and the second notification information indicating the details of the classification result. Depending on the resolution of the display unit, it may be difficult to sufficiently secure the display region for displaying the classification result. In this case, the first notification information is preferably simplified and displayed so as to be included in the size of the display region.

In a medical image processing apparatus according to a still another aspect of the present invention, the image acquiring unit preferably acquires time-series images as the medical image, and the storage preferably stores the time-series images and the second notification information or stores a still image included in the time-series images and the second notification information.

A medical image processing method according to a still another aspect of the present invention includes: a step of acquiring a medical image; a step of classifying, on the basis of the acquired medical image, the medical image or a region of interest included in the medical image; a step of generating, in accordance with a classification result of the classifying, first notification information for display and second notification information for storage, the second notification information differing from the first notification information; a step of causing a display unit to display the medical image and the first notification information; and a step of storing the medical image and the second notification information.

According to the present invention, by generating notification information in a plurality of forms for display and for storage in accordance with a classification result of a medical image, examinations using the medical image are not hindered, and a result for support based on the notification information can be sufficiently utilized.

BRIEF DESCRIPTION OF THE DRAWINGS

FIG. 4 is a table illustrating a relationship between a classification result and first notification information for display and second notification information for storage;

FIG. 5A illustrates a first embodiment of a notification form of a first composite image for display;

FIG. 5B illustrates a first embodiment of a notification form of a second composite image for storage;

FIG. 9 is a table illustrating a relationship between the classification result in accordance with the numbers of displays and storages and the first notification information for display and the second notification information for storage;

DESCRIPTION OF THE PREFERRED EMBODIMENTS

Now, preferred embodiments of a medical image processing apparatus and a medical image processing method according to the present invention will be described with reference to the accompanying drawings.

Figure 1:
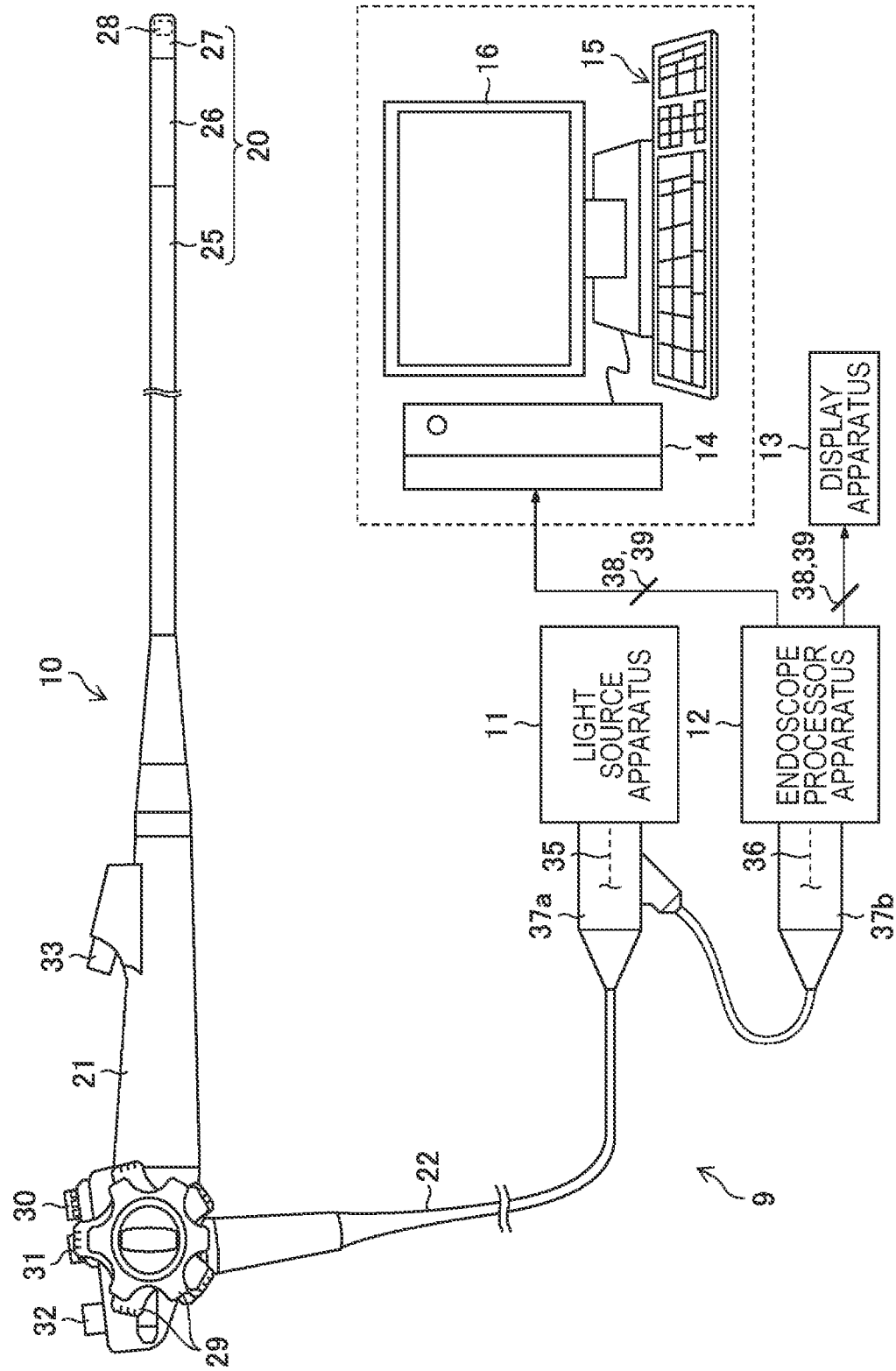
FIG. 1 is a schematic diagram illustrating an overall configuration of an endoscope system 9 including a medical image processing apparatus according to the present invention.

Overall Configuration of Endoscope System Including Medical Image Processing Apparatus FIG. 1 is a schematic diagram illustrating an overall configuration of an endoscope system 9 including the medical image processing apparatus according to the present invention.

As illustrated in FIG. 1, the endoscope system 9 includes an endoscope 10, which is an electronic endoscope, a light source apparatus 11, an endoscope processor apparatus 12, a display apparatus 13, a medical image processing apparatus 14, an operating unit 15, and a display 16.

The endoscope 10 captures time-series medical images including a photographic subject image and is a flexible endoscope, for example. The endoscope 10 has an insertion part 20, a handheld operating unit 21, and a universal cord 22. The insertion part 20 is inserted into a subject and has a distal end and a base end. The handheld operating unit 21 is disposed continuously with the base end side of the insertion part 20 and held by a surgeon to perform various operations. The universal cord 22 is disposed continuously with the handheld operating unit 21.

The entirety of the insertion part 20 is formed to have a small diameter and an elongated shape. The insertion part 20 is constituted by a soft part 25, a bending part 26, and a distal end part 27, which are disposed continuously with each other in this order from the base end side to the distal end side. The soft part 25 has flexibility. The bending part 26 is bendable by an operation of the handheld operating unit 21. An imaging optical system (objective lens), an imaging element 28, and the like, which are not illustrated, are incorporated in the distal end part 27.

The imaging element 28 is an imaging element of a CMOS (complementary metal oxide semiconductor) type or a CCD (charge coupled device) type. Image light of a part to be observed is incident on an imaging surface of the imaging element 28 through an observation window and the objective lens. The observation window, which is not illustrated, is open on a distal end surface of the distal end part 27, and the objective lens, which is not illustrated, is disposed behind the observation window. The imaging element 28 captures the image light of the part to be observed, which is incident on the imaging surface (converts the image light into an electric signal) and outputs an image signal.

The handheld operating unit 21 is provided with various operation members to be operated by a surgeon. Specifically, the handheld operating unit 21 is provided with two types of bending operation knobs 29 to be used for a bending operation of the bending part 26, an air/water supply button 30 for air supply/water supply operations, and a suction button 31 for a suction operation. The handheld operating unit 21 is further provided with a still image capturing instruction unit 32 for issuing an instruction for capturing a still image 39 of the part to be observed and a treatment tool introduction port 33 for inserting a treatment tool (not illustrated) into a treatment tool insertion path (not illustrated) that penetrates through the insertion part 20.

The universal cord 22 is a connection cord for connecting the endoscope 10 to the light source apparatus 11. The universal cord 22 contains a light guide 35 that penetrates through the insertion part 20, a signal cable 36, and a fluid tube (not illustrated). In addition, an end portion of the universal cord 22 is provided with a connector 37a that is connected to the light source apparatus 11 and a connector 37b that branches off from the connector 37a and is connected to the endoscope processor apparatus 12.

Since the connector 37a is connected to the light source apparatus 11, the light guide 35 and the fluid tube (not illustrated) are inserted into the light source apparatus 11. Thus, through the light guide 35 and the fluid tube (not illustrated), necessary illumination light, water, and gas are supplied from the light source apparatus 11 to the endoscope 10. As a result, the part to be observed is irradiated with the illumination light from an illumination window (not illustrated) on the distal end surface of the distal end part 27. In accordance with a pressing operation on the air/water supply button 30 described above, the gas or water is injected from an air/water supply nozzle (not illustrated) on the distal end surface of the distal end part 27 to the observation window (not illustrated) on the distal end surface.

Since the connector 37b is connected to the endoscope processor apparatus 12, the signal cable 36 is electrically connected to the endoscope processor apparatus 12. Thus, through the signal cable 36, an image signal of the part to be observed is output from the imaging element 28 of the endoscope 10 to the endoscope processor apparatus 12, and also, a control signal is output from the endoscope processor apparatus 12 to the endoscope 10.

The light source apparatus 11 supplies the illumination light through the connector 37a to the light guide 35 of the endoscope 10. As the illumination light, special light in various wavelength ranges in accordance with an observation purpose, such as white light (light in a white wavelength range or light in a plurality of wavelength ranges), light in one or more specific wavelength ranges, or a combination thereof is selected. Note that the specific wavelength range is narrower than the white wavelength range.

The special light in various wavelength ranges includes special light for a special-light image (BLI (Blue Light Imaging or Blue LASER Imaging), LCI (Linked Color Imaging), or NBI (Narrow Band Imaging)).

The illumination light for BLI is illumination light having a high proportion of violet light with high absorbance for a superficial blood vessel whereas the proportion of green light with high absorbance for a middle blood vessel is reduced, and is suitable for generating an image (BLI) suitable for enhancing a blood vessel or a structure in a mucosal superficial layer of a subject.

The illumination light for LCI is illumination light in which the proportion of violet light is higher than that of white light and which is more suitable for capturing a fine change in color tone than the white light, and is suitable for generating an image (LCI) subjected to color enhancement processing to make a reddish color more red and a whitish color more white relative to the color near the mucous membrane by also using the signal of a red component.

The illumination light for NBI is suitable for generating an image (NBI) in which a fine change in the surface to be irradiated is enhanced by narrowing the range of the wavelengths of illumination light to be applied.

A first example of the specific wavelength range is, for example, a blue range or a green range in a visible range. The wavelength range of the first example includes a wavelength range of greater than or equal to 390 nm and less than or equal to 450 nm or greater than or equal to 530 nm and less than or equal to 550 nm, and light of the first example has a peak wavelength in the wavelength range of greater than or equal to 390 nm and less than or equal to 450 nm or greater than or equal to 530 nm and less than or equal to 550 nm.

A second example of the specific wavelength range is, for example, a red range in a visible range. The wavelength range of the second example includes a wavelength range of greater than or equal to 585 nm and less than or equal to 615 nm or greater than or equal to 610 nm and less than or equal to 730 nm, and light of the second example has a peak wavelength in the wavelength range of greater than or equal to 585 nm and less than or equal to 615 nm or greater than or equal to 610 nm and less than or equal to 730 nm.

A third example of the specific wavelength range includes a wavelength range in which oxidized hemoglobin and reduced hemoglobin have different absorption coefficients, and light of the third example has a peak wavelength in the wavelength range in which oxidized hemoglobin and reduced hemoglobin have different absorption coefficients. The wavelength range of the third example includes a wavelength range of 400±10 nm, 440±10 nm, 470±10 nm, or greater than or equal to 600 nm and less than or equal to 750 nm, and light of the third example has a peak wavelength in the wavelength range of 400±10 nm, 440±10 nm, 470±10 nm, or greater than or equal to 600 nm and less than or equal to 750 nm.

A fourth example of the specific wavelength range is the wavelength range (from 390 nm to 470 nm) of excitation light that is used for observing fluorescence (fluorescence observation) emitted by a fluorescent material in a living body and that excites the fluorescent material.

A fifth example of the specific wavelength range is the wavelength range of infrared light. The wavelength range of the fifth example includes a wavelength range of greater than or equal to 790 nm and less than or equal to 820 nm or greater than or equal to 905 nm and less than or equal to 970 nm, and light of the fifth example has a peak wavelength in the wavelength range of greater than or equal to 790 nm and less than or equal to 820 nm or greater than or equal to 905 nm and less than or equal to 970 nm.

The endoscope processor apparatus 12 controls operations of the endoscope 10 through the connector 37b and the signal cable 36. In addition, on the basis of the image signal acquired from the imaging element 28 of the endoscope 10 through the connector 37b and the signal cable 36, the endoscope processor apparatus 12 generates an image (also referred to as "moving image 38") formed of time-series frame images 38a including a photographic subject image. Furthermore, if the still image capturing instruction unit 32 is operated in the handheld operating unit 21 of the endoscope 10, concurrently with the generation of the moving image 38, the endoscope processor apparatus 12 sets one frame image in the moving image 38 as the still image 39 in accordance with the timing of an imaging instruction.

The moving image 38 and the still image 39 are medical images obtained by capturing images of the inside of the subject, that is, a living body. In addition, if the moving image 38 and the still image 39 are images obtained with the above-described light in the specific wavelength range (special light), both are special-light images. In addition, the endoscope processor apparatus 12 outputs the generated moving image 38 and the still image 39 to each of the display apparatus 13 and the medical image processing apparatus 14.

Note that the endoscope processor apparatus 12 may generate (acquire) the special-light image having information on the above-described specific wavelength range, on the basis of a usual-light image obtained with the above-described white light. In this case, the endoscope processor apparatus 12 functions as a special-light image acquiring unit. Then, the endoscope processor apparatus 12 obtains a signal in the specific wavelength range by performing calculation based on RGB (Red, Green, Blue) color information or CMY (Cyan, Magenta, Yellow) color information included in the usual-light image.

On the basis of, for example, at least one of the usual-light image obtained with the above-described white light or the special-light image obtained with the above-described light in the specific wavelength range (special light), the endoscope processor apparatus 12 may generate a feature quantity image such as a known oxygen saturation image. In this case, the endoscope processor apparatus 12 functions as a feature quantity image generating unit. Note that each of the moving image 38 and the still image 39 including the above-described in-living-body image, the usual-light image, the special-light image, and the feature quantity image is a medical image obtained by converting results of imaging or measuring of a human body into an image for the purpose of image diagnosis or examination.

The display apparatus 13 is connected to the endoscope processor apparatus 12 and functions as a display unit that displays the moving image 38 and the still image 39 input from the endoscope processor apparatus 12. A user (physician) operates the insertion part 20 back and forth, for example, while viewing the moving image 38 displayed on the display apparatus 13, and, if a lesion or the like is found at the part to be observed, the user (physician) operates the still image capturing instruction unit 32 to capture a still image of the part to be observed for diagnosis, biopsy, or the like.

Medical Image Processing Apparatus

Mainly, the medical image processing apparatus 14 classifies a medical image that is being captured or a region of interest that is included in the medical image into any of two or more classes on the basis of time-series medical images and notifies a user of the classification result. In this embodiment, for example, a personal computer is used. In addition, a keyboard, a mouse, and the like connected to the personal computer with or without wires are used for the operating unit 15, and any type of monitor, such as a liquid crystal monitor, which can be connected to the personal computer is used as the display (display unit) 16.

Figure 2:
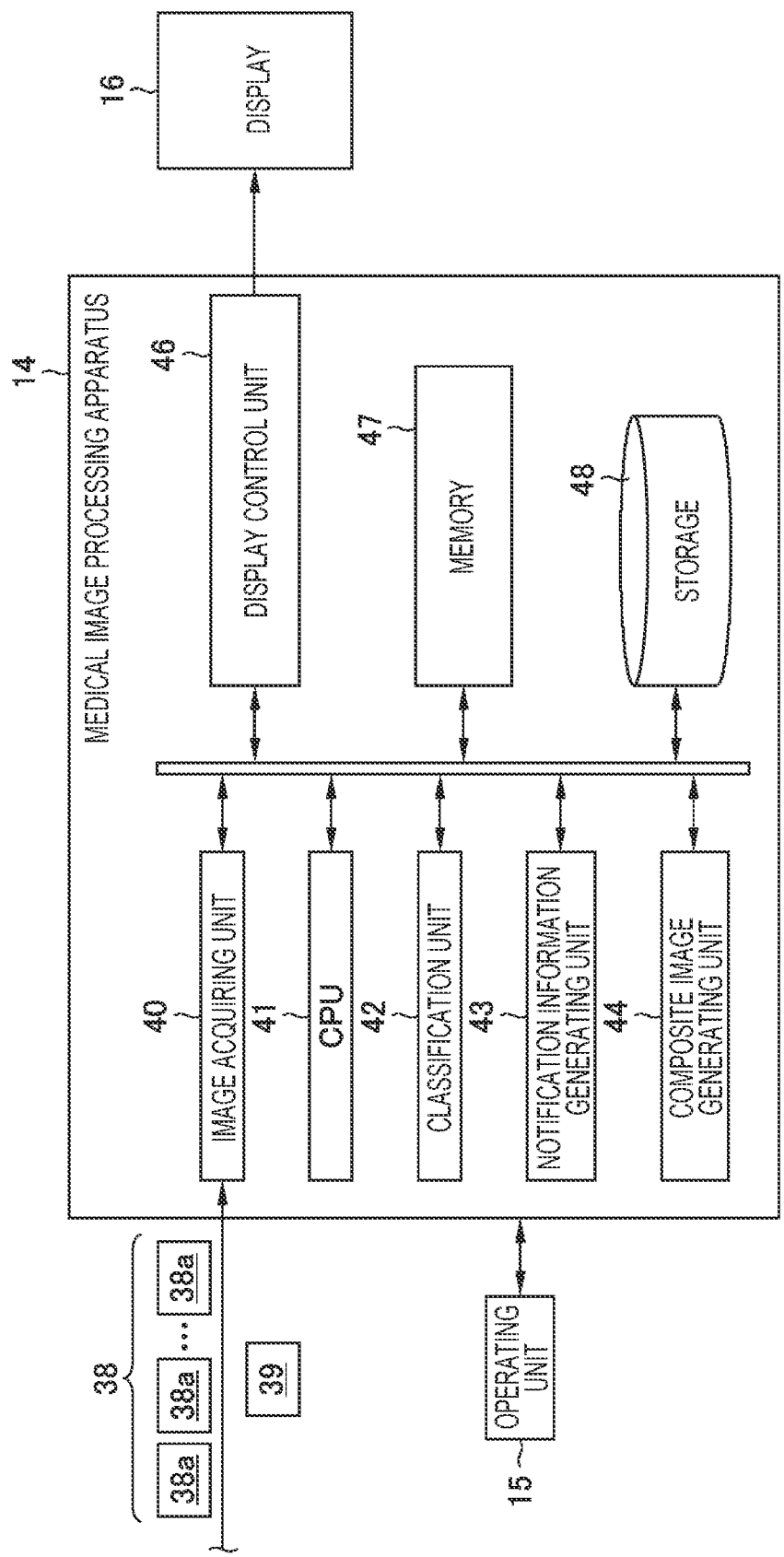
FIG. 2 is a block diagram illustrating an embodiment of a medical image processing apparatus 14.

FIG. 2 is a block diagram illustrating an embodiment of the medical image processing apparatus 14.

The medical image processing apparatus 14 illustrated in FIG. 2 is mainly constituted by an image acquiring unit 40, a CPU (Central Processing Unit) 41, a classification unit 42, a notification information generating unit 43, a composite image generating unit 44, a display control unit 46, a memory 47, and a storage 48.

The CPU 41 operates on the basis of a program stored in the memory 47 and generally controls the image acquiring unit 40, the classification unit 42, the notification information generating unit 43, the composite image generating unit 44, the display control unit 46, and the storage 48. The CPU 41 also functions as part of these units.

By using an image input/output interface (not illustrated) that is connected to the endoscope processor apparatus 12 (FIG. 1) with or without wires, the image acquiring unit 40 acquires an image formed of the time-series frame images 38a (in this example, the moving image 38 captured by the endoscope 10) including a photographic subject image from the endoscope processor apparatus 12. In addition, if the endoscope 10 captures the above-described still image 39 while capturing the moving image 38, the image acquiring unit 40 acquires the moving image 38 and the still image 39 from the endoscope processor apparatus 12.

On the basis of the time-series frame images 38a acquired by the image acquiring unit 40, the classification unit 42 acquires a feature quantity of the frame images 38a. On the basis of the acquired feature quantity, the classification unit 42 classifies each of the frame images 38a or a region of interest included in each of the frame images 38a into any of two or more classes.

In this example, as will be described later, the two or more classes are three classes, which are "nonneoplastic", "neoplastic", and "other".

In accordance with the classification result of the frame images 38a or the region of interest classified by the classification unit 42, the notification information generating unit 43 generates first notification information for display and second notification information for storage, the second notification information differing from the first notification information. Note that details of the notification information generating unit 43 will be described later.

The composite image generating unit 44 generates a composite image (first composite image for display) in which the frame images 38a and first notification information for display generated in accordance with the classification result of the frame images 38a are composited, and generates a composite image (second composite image for storage) in which the frame images 38a and second notification information for storage generated in accordance with the classification result of the frame images 38a are composited.

The display control unit 46 generates image data for display on the basis of a medical image (the moving images 38, the still image 39) acquired by the image acquiring unit 40 and outputs the image data for display to the display 16. However, if the first composite image for display is generated by the composite image generating unit 44, the display control unit 46 preferentially outputs image data of the first composite image for display to the display 16.

Thus, the medical image is displayed on the display 16. In addition, for a medical image having a region of interest such as a lesion, the first notification information for display (i.e., the first composite image for display) indicating the classification result of the medical image or the region of interest is displayed.

The memory 47 functions as a work area of the CPU 41 or functions as a memory that stores an operating system, various programs such as a medical image processing program, a table indicating a relationship between the classification result of the medical image and the first notification information and the second notification information corresponding to the classification result, and the like.

The storage 48 stores the moving image 38 and the still image 39 that are captured. However, if the second composite image for storage is generated by the composite image generating unit 44, the storage 48 preferentially stores the second composite image for storage.

Classification Unit

Next, an embodiment of the classification unit 42 will be described.

The classification unit 42 in this example calculates a feature quantity from images (frame images 38a), includes a convolutional neural network (CNN) that performs image recognition processing, and calculates the feature quantity by using color information, a pixel value gradient, or the like in the images. On the basis of the calculated feature quantity, the classification unit 42 classifies an image (medical image) or a region of interest included in the image into any of a plurality of classes, such as "nonneoplastic", "neoplastic", and "other" in this example.

Figure 3:
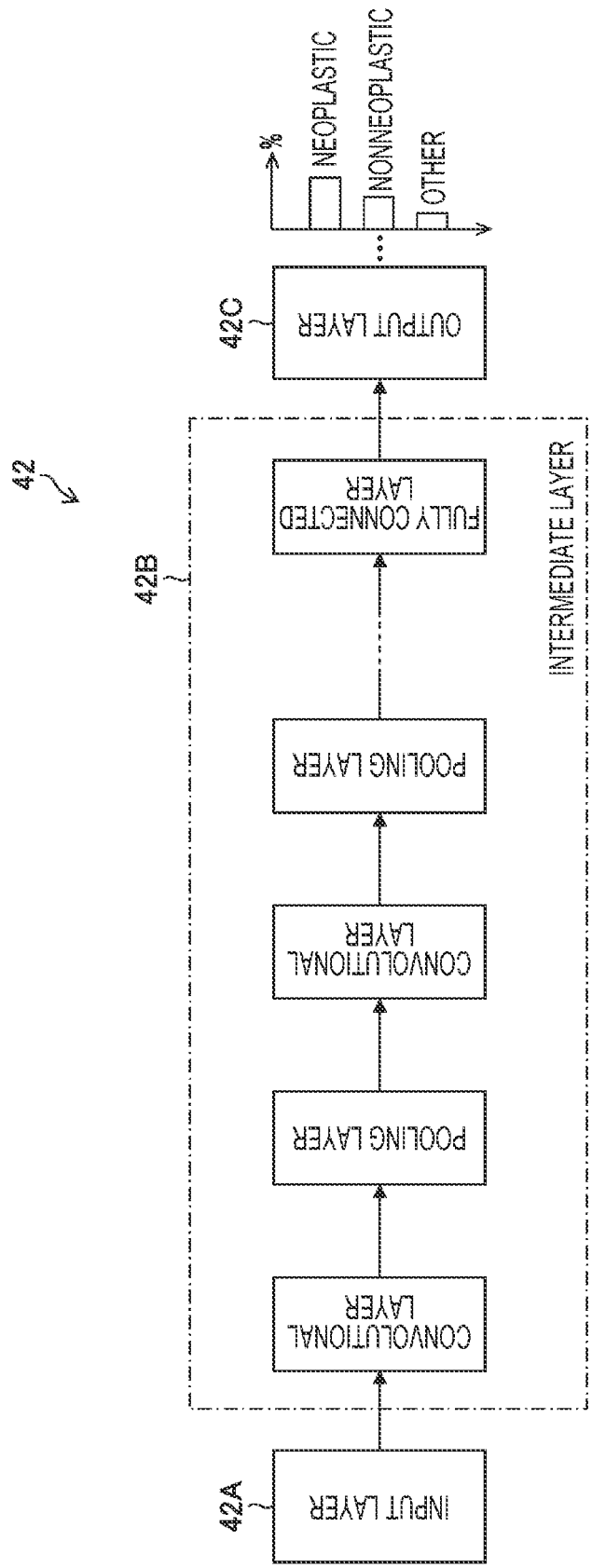
FIG. 3 is a schematic diagram illustrating a typical configuration example of a CNN applied in a classification unit 42 in this example.

FIG. 3 is a schematic diagram illustrating a typical configuration example of the CNN applied in the classification unit 42 in this example.

As illustrated in FIG. 3, the classification unit (CNN) 42 includes an input layer 42A, an intermediate layer 42B, and an output layer 42C. The intermediate layer 42B has a plurality of sets, each including a convolutional layer and a pooling layer, and a fully connected layer. Each layer has a structure in which a plurality of "nodes" are coupled using "edges".

The frame images 38a of the moving image 38 are sequentially input to the input layer 42A.

The intermediate layer 42B has a plurality of sets, in which a convolutional layer and a pooling layer are one set, and a fully connected layer, and extracts a feature quantity from the frame images 38a input from the input layer. The convolutional layer performs filtering processing (performs a convolution operation using a filter) on a nearby node in the preceding layer to acquire a "feature map". The pooling layer reduces the feature map output from the convolutional layer to obtain a new feature map. The "convolution layer" plays a role of feature extraction such as edge extraction from an image, and the "pooling layer" plays a role of providing robustness so that the extracted features are not affected by parallel displacement or the like.

Note that the intermediate layer 42B includes, not only each set of the convolutional layer and the pooling layer, but also consecutive convolutional layers or a normalization layer.

The fully connected layer is a portion that is weight-connected to all nodes in the preceding layer and that outputs a value (feature variable) converted by an activation function. In this example, the fully connected layer outputs a feature variable for each classification of the frame images 38a or the region of interest such as a lesion included in the frame images 38a.

The output layer 42C functioning as an inference unit converts output (feature variable) from the fully connected layer into a probability by using a softmax function and calculates a score (probability) for each class to be classified. In this example, since the frame images 38a or the region of interest is classified into any of the three classes, which are "nonneoplastic", "neoplastic", and "other", the output layer 42C outputs a class with a largest score among the scores in the three classes (the total of the three scores is 100%) and the score in the class as the classification result.

Note that parameters of a filter used in each convolutional layer, a weighting factor of the fully connected layer, and the like in the intermediate layer 42B are optimized in advance by using a large number of pieces of training data.

FIG. 4 is a table illustrating a relationship between the classification result and the first notification information for display and the second notification information for storage.

In the example illustrated in FIG. 4, if the classification result of a medical image or a region of interest included in the medical image is "nonneoplastic", the first notification information for display is text information "NN", and the second notification information for storage is text information "nonneoplastic".

If the classification result is "neoplastic", the first notification information for display is text information "N", and the second notification information for storage is text information "neoplastic". If the classification result is "other", the first notification information for display is text information "O", and the second notification information for storage is text information "other".

In the example illustrated in FIG. 4, the first notification information for display is the first letter of the second notification information for storage. If the first letters of different classification results are common, the first notification information for display is at least distinguishable, simplified text information.

The first notification information may be freely set by a user or may be automatically generated from the second notification information in accordance with a preset rule. In addition, a table illustrating a relationship between the classification result and the first notification information for display and the second notification information for storage, such as the table illustrated in FIG. 4, may be prepared, and a user may freely set the first notification information and the second notification information on the table by using the operating unit 15.

First Embodiment of Notification Form

FIGS. 5A and 5B illustrate first embodiments of notification forms of the first composite image for display and the second composite image for storage, respectively.

As described above, the composite image generating unit 44 generates the first composite image for display (see FIG. 5A) in which the frame images 38a and the first notification information for display generated in accordance with the classification result of the frame images 38a are composited, and generates the second composite image for storage (see FIG. 5B) in which the frame images 38a and the second notification information for storage generated in accordance with the classification result of the frame images 38a are composited.

FIGS. 5A and 5B illustrate examples of the first composite image for display and the second composite image for storage in a case where the classification result "neoplastic" is obtained by the classification unit 42.

The first notification information for display in a case where the classification result "neoplastic" is obtained is the text information "N" as illustrated in FIG. 4. Thus, the first composite image illustrated in FIG. 5A is a composite of the medical image and the text information "N" indicating the classification result (result).

On the other hand, the second notification information for storage in a case where the classification result "neoplastic" is obtained is the text information "neoplastic" as illustrated in FIG. 4. Thus, as illustrated in FIG. 5B, the second composite image is a composite of the medical image and the text information "neoplastic" indicating the classification result (result). Note that, in this example, information ("70%") on the degree of reliability (score) of "neoplastic" classified as a lesion is composited in the second composite image for storage as illustrated in FIG. 5B, but information on the degree of reliability of "neoplastic" is not composited in the first composite image for display.

The first composite image for display is displayed on the display 16 during endoscopy and can be observed by a user (physician) and a patient. The first composite image for display is displayed in real time but is not stored.

The user can perform endoscopy on the basis of a medical image included in the first composite image displayed on the display 16 and also can utilize the first notification information (text information "N" indicating the classification result) included in the first composite image for endoscopy.

Note that, on the basis of the first notification information "N", the user can recognize the classification result of the medical image or the region of interest obtained by the classification unit 42, whereas a person (patient) other than the user is unable to recognize the meaning of the first notification information "N". That is, the first notification information "N" is information in a notification form by which the classification result is not conveyed directly to the patient and is not recognized as information that makes the patient feel anxious.

In addition, in the example illustrated in FIG. 4, if the classification result is "other", the first notification information for display is the text information "O", and the second notification information for storage is the text information "other". However, the first notification information for display may also be the text information "other" because, if the classification result is "other", the patient is not made to feel anxious unnecessarily even if recognizing this. That is, in accordance with the classification result, the first notification information for display and the second notification information for storage may be made to differ from each other or may be made identical with each other.

On the other hand, if the form is recognizable only by the user who performs examination, as in the first notification information "N", it may be difficult to obtain understanding of experts or other physicians at a conference or the like. Thus, the second notification information for storage is information in a notification form that is understandable by such experts and the like (the text information "neoplastic" in this example). In the example illustrated in FIG. 5B, information ("70%") on the degree of reliability of the classification result is further added.

The second composite image for storage including the second notification information for storage is stored in the storage 48. The second composite image that is stored is a moving image in which the second notification information is composited for each frame. However, only a frame at which a still image capturing instruction is issued during endoscopy and a composite image of a still image in which the second notification information for the frame is composited may be stored in the storage 48.

The classification unit 42 classifies the medical image or the region of interest into any class of "nonneoplastic", "neoplastic", and "other" in the above embodiment. However, the classes for classification are not limited to those. Examples include endoscopic findings classification such as the NICE (NBI International Colorectal Endoscopic) classification or the JNET (The Japan NBI Expert Team) classification, disease type classification (e.g., hyperplastic polyp, adenoma, intramucosal cancer, high-level invasive cancer, or inflammatory polyp), classification based on the shape, size, position, or the like of the lesion, and classification based on the degree of reliability or seriousness of the classification result of the lesion part, and classification combining these.

If an endoscopic image is an image captured under special light for NBI, the classification unit 42 can classify the endoscopic image in accordance with the NICE classification or the JNET classification. It is needless to say that the first notification information for display and the second notification information for storage in accordance with the classification result differ depending on the classification method.

In addition, elements of the form of the notification information are not limited to words and numeric values as in the above case and include a figure, color, position, and the like.

Modification of First Embodiment of Notification Form

Figure 6A:
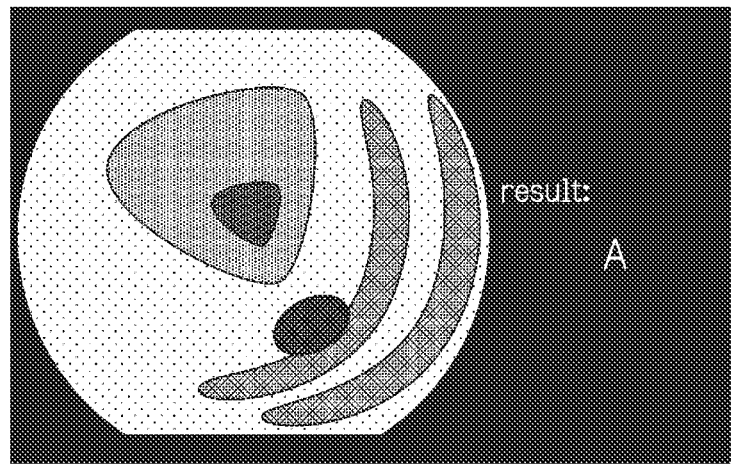
FIG. 6A illustrates a modification of the first embodiment of the notification form of the first composite image for display.
Figure 6B:
FIG. 6B illustrates a modification of the first embodiment of the notification form of the second composite image for storage.

FIGS. 6A and 6B illustrate modifications of the first embodiments of the notification forms of the first notification information and the second notification information and illustrate the first composite image for display and the second composite image for storage in a case where the classification unit 42 classifies a medical image or a region of interest into "Type 2" according to the NICE classification.

Since "Type 2" according to the NICE classification is a pathology that is most likely to be the "adenoma", the first notification information for display is the text information "A", which is the first letter of "adenoma". Thus, as illustrated in FIG. 6A, the first composite image for display is a composite of the medical image and the text information "A".

On the other hand, the second notification information for storage in a case where the classification result of "Type 2" according to the NICE classification is obtained is the text information "adenoma". Thus, as illustrated in FIG. 6B, the second composite image for storage is a composite of the medical image and the text information "adenoma".

In the above manner, according to the modification of the first embodiment of the notification form, as in the first embodiment of the notification form, the first notification information for display is information in a notification form by which the patient does not directly understand the classification result, and the second notification information for storage is information in a notification form that is understandable by experts and the like.

Second Embodiment of Notification Form

Figure 7A:
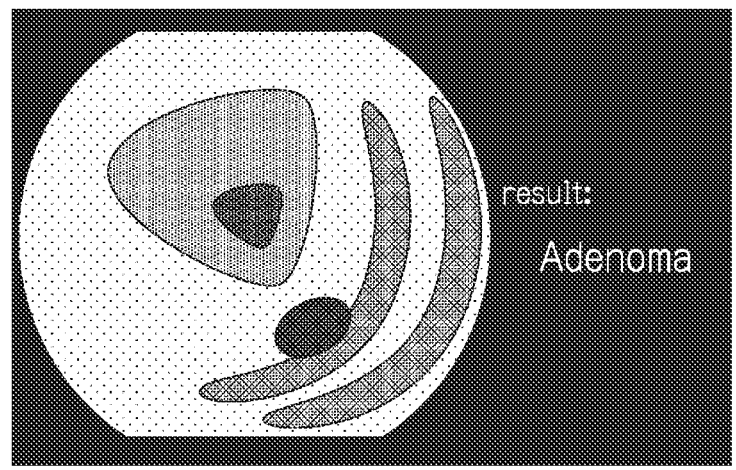
FIG. 7A illustrates a second embodiment of the notification form of the first composite image for display.
Figure 7B:
FIG. 7B illustrates a second embodiment of the notification form of the second composite image for storage.

FIGS. 7A and 7B illustrate second embodiments of the notification forms of the first notification information and the second notification information and illustrate the first composite image for display and the second composite image for storage in a case where the classification unit 42 classifies a medical image or a region of interest into "Type 2" according to the NICE classification.

In a case of classification into "Type 2" according to the NICE classification, if the classification result is obtained as having a high degree of reliability of the "adenoma" (highly cancerous), the first notification information for display is the text information "adenoma" in a color that does not draw attraction (e.g., achromatic color). Thus, as illustrated in FIG. 7A, the first composite image for display is a composite of the medical image and the first notification information for display (the text information "adenoma" in a color that does not draw attention).

On the other hand, the second notification information for storage in a case where the classification result of "Type 2" according to the NICE classification is obtained is the text information "adenoma" in a color that draws attention, such as red. Thus, as illustrated in FIG. 7B, the second composite image for storage is a composite of the medical image and the text information "adenoma" in a color that draws attention.

In the above manner, according to the second embodiments of the notification forms, if the classification result with a high degree of reliability of a lesion (highly cancerous) is obtained, the first notification information for display is text information in a color that does not draw attention, whereas the second notification information for storage is text information in a color that draws attention.

Thus, even if the patient sees the first composite image displayed on the display 16, the patient can be prevented from knowing a cancerous property or the like of a lesion and can be prevented from feeling anxious.

The information for drawing the user's attention is not limited to the color of the text information and may be addition of numeric value information on the degree of reliability of the lesion, the size and position of the text information, and the like.

Third Embodiment of Notification Form

Figure 8A:
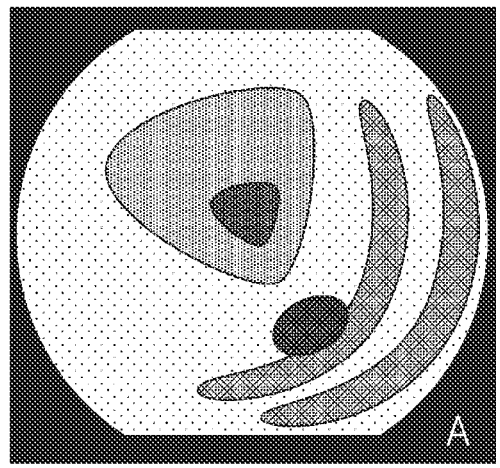
FIG. 8A illustrates a third embodiment of the notification form of the first composite image for display.
Figure 8B:
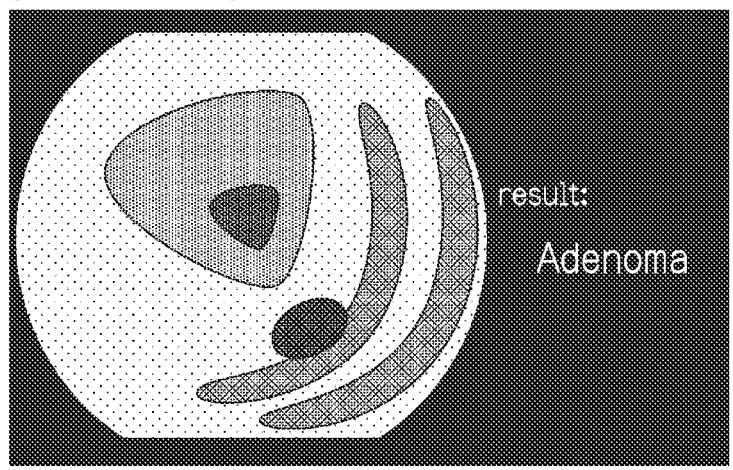
FIG. 8B illustrates a third embodiment of the notification form of the second composite image for storage.

FIGS. 8A and 8B illustrate third embodiments of the notification forms of the first notification information and the second notification information and illustrate the first composite image for display and the second composite image for storage in a case where the classification unit 42 classifies a medical image or a region of interest into "Type 2" according to the NICE classification.

The notification information generating unit 43 acquires resolution information of the display to which the first composite image for display is to be output.

In a case where the resolution of the display is low, if the image size of the medical image is reduced, diagnosis is adversely affected. Thus, the medical image is preferably displayed with the image size at the time of image capturing. Thus, in a case where the resolution of the display is low, the medical image is displayed on the entire screen of the display, and as a result, it may be difficult to sufficiently secure a display region for displaying the first notification information for display in accordance with the classification result.

Thus, on the basis of the resolution information of the display acquired from the display, the notification information generating unit 43 acquires the display region of the classification result, and generates the first notification information for display in which details of the classification result are simplified to correspond to the size of the display region.

According to the third embodiment of the notification form illustrated in FIG. 8A, in the first notification information for display in a case of classification into "Type 2" according to the NICE classification, "adenoma" is simplified to only the first letter thereof, "A".

In addition, the composite image generating unit 44 uses a lower right region of the screen of the display as the display region of the classification result, and generates the first composite image for display in which "A" is composited in the display region.

On the other hand, according to the third embodiment of the notification form illustrated in FIG. 8B, the second notification information for storage in a case where the classification result of "Type 2" according to the NICE classification is obtained is not affected by the resolution of the display, the second notification information indicates the details of the classification result (text information "adenoma" that is not simplified).

In addition, the composite image generating unit 44 generates the second composite image for display in which the text information "adenoma" is composited in substantially the center of a right region of the medical image.

That is, the size of the first notification information for display may be limited by the resolution of the display. In such a case, the first notification information for display itself is simplified so as to reduce the size of the first notification information. On the other hand, the second notification information for storage is not necessarily correspond to the size of the display, and thus, the size of the second notification information is not reduced in accordance with the classification result, and the second notification information indicates details of the classification result.

In the example illustrated in FIGS. 8A and 8B, in the first notification information, "adenoma" is simplified to the first letter thereof, "A". However, without limitation to simplification of the text information, in a case where a plurality of pieces of information are included as the classification result, the plurality of pieces of information may be narrowed down to only necessary information so as to simplify the information amount for display.

Notification Form in Accordance With Numbers of Displays and Storages

FIG. 9 is a table illustrating a relationship between the classification result in accordance with the numbers of displays and storages and the first notification information for display and the second notification information for storage, and illustrates a case where two displays and two storages are provided.

Depending on a facility, a display for a patient and a display for a user may be separate, or the same display may be seen during examination. In addition, at the time of storage, information for the facility and information for a conference or the like may be wished to be separately stored.

Two types of first notification information for display and two types of second notification information for storage illustrated in FIG. 9 are a case where the classification unit 42 classifies a medical image or a region of interest into classification results "1", "2", "3", "4", . . . .

The classification results "1", "2", and "3" indicate cases of classification into "Type 1", "Type 2", and "Type 3" according to the NICE classification, respectively. The classification result "4" indicates a case of classification into "Adenoma" and the degree of reliability "70%".

Second notification information for storage 1 corresponding to the classification results "1", "2", "3", and "4" is "Hyperplastic", "Adenoma", "Malignancy", and red-letter "Adenoma", which are most likely pathologies indicated by "Type 1", "Type 2", and "Type 3" according to the NICE classification, and first notification information for display 1 corresponding to this is first letters of the text information, "H", "A", "M", and "A".

Second notification information for storage 2 corresponding to the classification results "1", "2", "3", and "4" is "NICE Classification Type 1", "NICE Classification Type 2", "NICE Classification Type 3", and "Adenoma 70%", and first notification information for display 2 corresponding to this is "Type A", "Type B", "Type C", and achromatic "Adenoma".

Here, although the first notification information for display 2 corresponding to the second notification information for storage 2 in accordance with the classification results "1", "2", and "3" are "Type A", "Type B", and "Type C", since the classification method and the meanings of "Type A", "Type B", and "Type C" of the first notification information are unknown, a person (patient) other than the user is unable to recognize the classification results. The first notification information for display 2 corresponding to the second notification information for storage 2 in accordance with the classification result "4" is achromatic "Adenoma", and also, the numerical values of the degree of reliability are omitted, thereby preventing the patient from feeling anxious.

Although the example illustrated in FIG. 9 is a case where two displays and two storages are provided, at least one of the number of displays or the number of storages may be two or more. In addition, the notification information generating unit 43 generates a plurality of types of first notification information whose upper limit equals to the total number of a plurality of displays if a plurality of displays are provided, and generates a plurality of types of second notification information whose upper limit equals to the total number of a plurality of storages if a plurality of storages are provided.

Figure 10A:
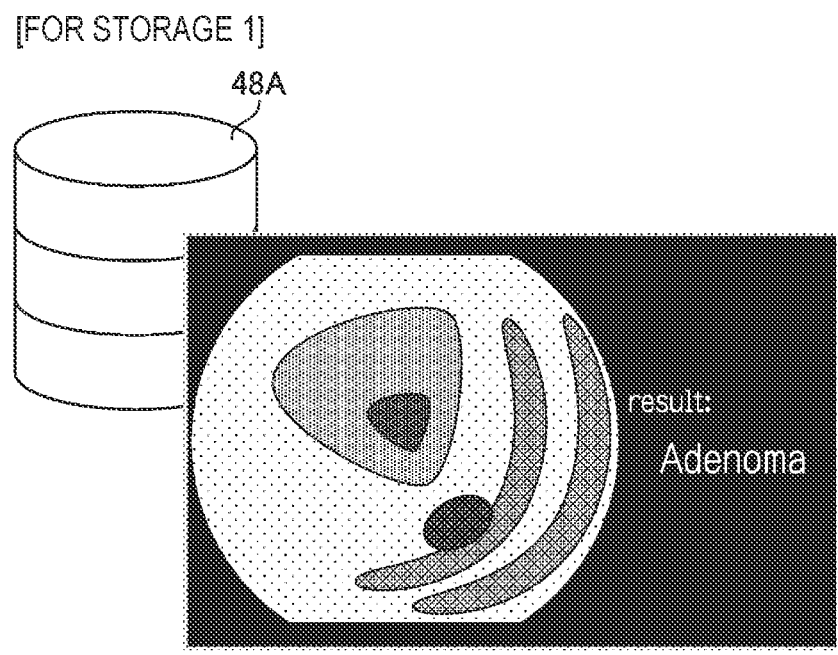
FIG. 10A illustrates a composite image for storage 1 in which second notification information for storage 1 is composited.
Figure 10B:
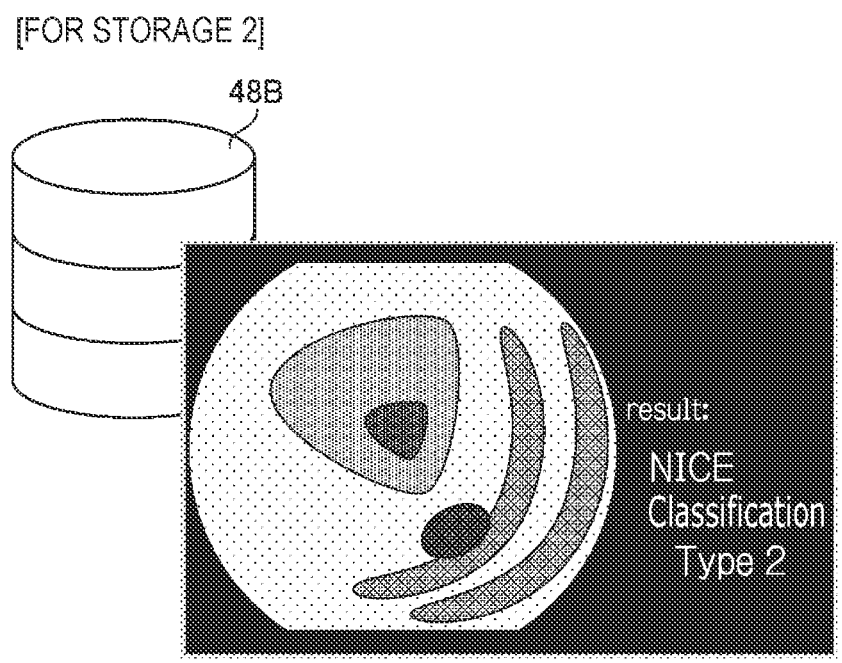
FIG. 10B illustrates a composite image for storage 2 in which second notification information for storage 2 is composited.

FIGS. 10A and 10B illustrate composite images for storage 1 and 2 in which the second notification information for storage 1 and 2 are composited, respectively. The composite image for storage 1 is stored in a storage 48A, and the composite image for storage 2 is stored in a storage 48B. Note that the storages 48A and 48B may be physically different storages or may be different storage regions in the storage 48 (FIG. 2).

Figure 11A:
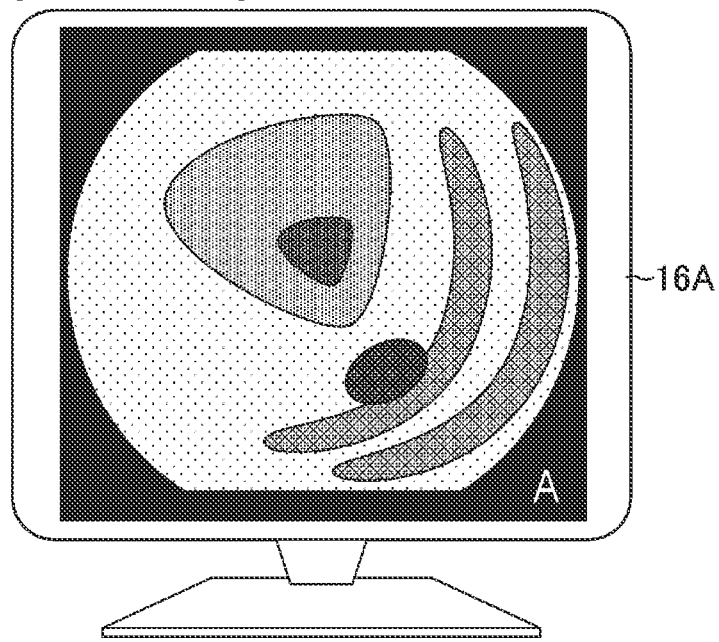
FIG. 11A illustrates a composite image for display 1 in which first notification information for display 1 is composited.
Figure 11B:
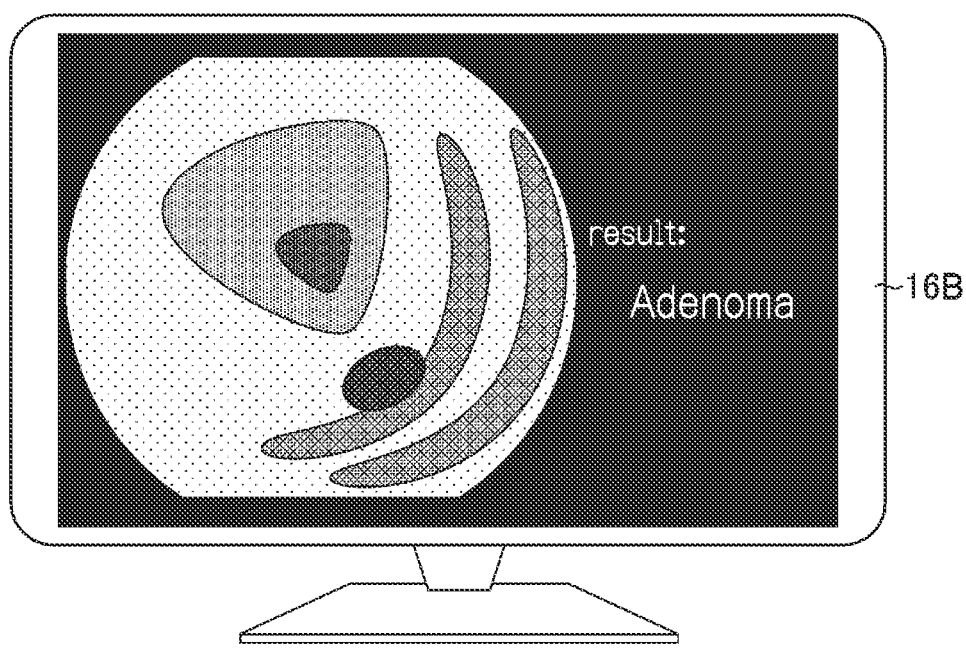
FIG. 11B illustrates a composite image for display 2 in which first notification information for display 2 is composited.

FIGS. 11A and 11B illustrate composite images for display 1 and 2 in which the first notification information for display 1 and 2 are composited, respectively. The composite image for display 1 is displayed on a display 16A, and the composite image for display 2 is displayed on a display 16B.

Medical Image Processing Method

Figure 12:
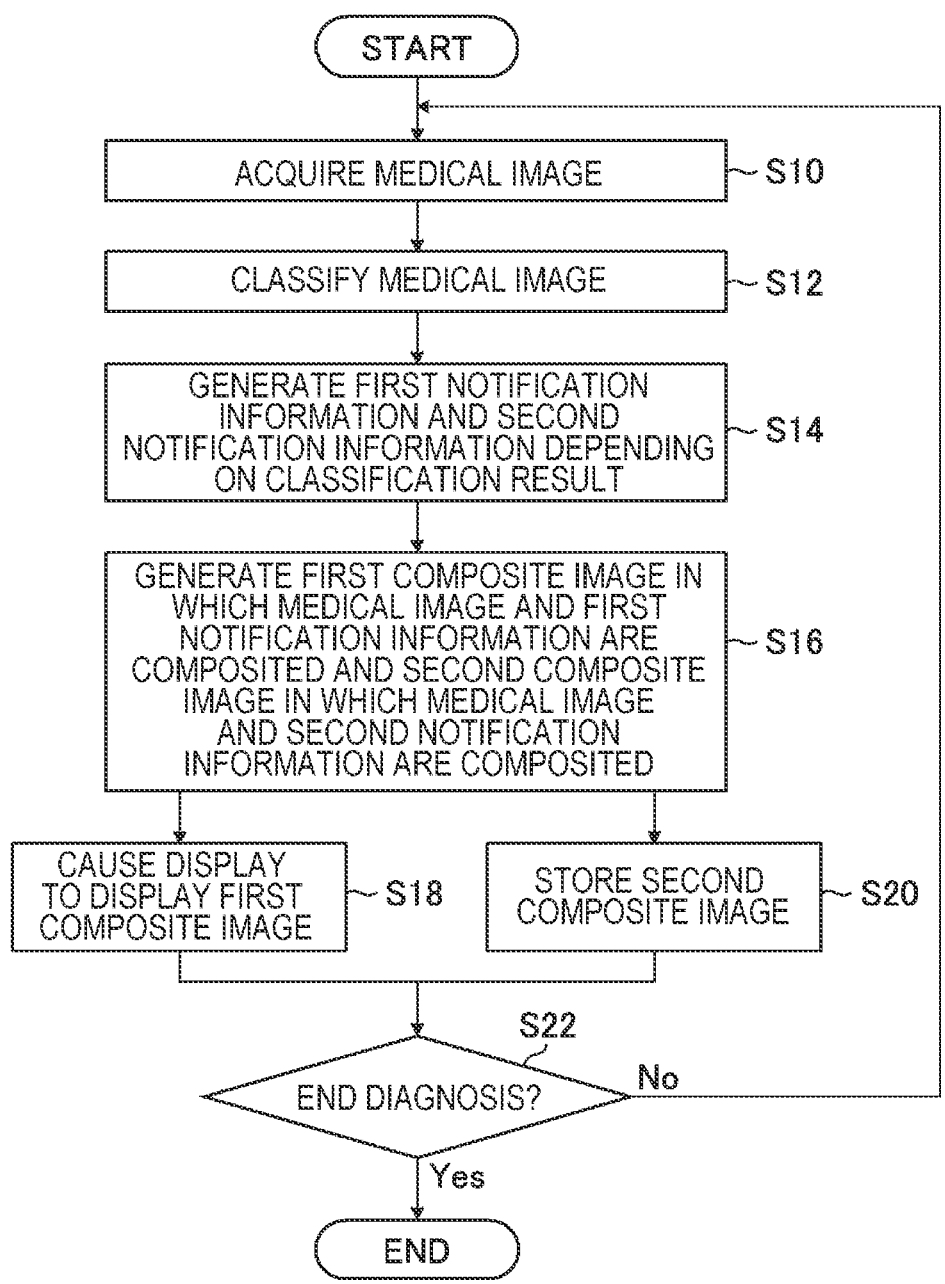
FIG. 12 is a flowchart illustrating an embodiment of a medical image processing method according to the present invention.

FIG. 12 is a flowchart illustrating an embodiment of the medical image processing method according to the present invention, and illustrates a processing procedure of each unit of the medical image processing apparatus 14 illustrated in FIG. 2.

In FIG. 12, the image acquiring unit 40 acquires one-frame medical image among time-series medical images that are a processing target from the endoscope processor apparatus 12 (step S10).

From the medical image acquired in step S10, the classification unit 42 obtains a feature quantity of the medical image, and, on the basis of the feature quantity, the classification unit 42 classifies the medical image or a region of interest included in the medical image into any of two or more classes (step S12). For example, in the example illustrated in FIG. 4, the medical image or the region of interest is classified into any of the plurality of classes, which are "nonneoplastic", "neoplastic", and "other".

In accordance with the classification result of the medical image or the region of interest obtained by the classification unit 42, the notification information generating unit 43 generates first notification information for display and second notification information for storage (step S14). Although the second notification information for storage is text information "nonneoplastic", "neoplastic", or "other" in accordance with the classification result "nonneoplastic", "neoplastic", or "other" as illustrated in FIG. 4, the first notification information for display is "NN", "N", or "O" as abbreviation for the second notification information, and a person (patient) other than the user is not able to recognize the classification result indicated by the first notification information for display.

The composite image generating unit 44 generates a first composite image for display, which is a composite of the medical image and the first notification information, and generates a second composite image for storage, which is a composite of the medical image and the second notification information (step S16).

The display control unit 46 causes the display 16 to display the first composite image for display (step S18), and the storage 48 stores the second composite image for storage (step S20).

Subsequently, the CPU 41 determines whether an instruction for ending endoscopic image diagnosis (or ending image capturing) is issued from the operating unit 15 (step S22). If no instruction for ending diagnosis is issued ("No"), the CPU 41 advances to step S10 and performs processing on the following-frame medical image from step S10 to step S22. If an instruction for ending diagnosis is issued ("Yes"), the CPU 41 ends the processing.

Miscellaneous

The classification unit according to the present invention may, not only classify a medical image or a region of interest included in the medical image by a learner such as a CNN, but also detect the region of interest by analyzing, through image processing, a feature quantity in the medical image, such as a color, a pixel value gradient, a shape, or a size, and classify, on the basis of the feature quantity of the detected region of interest, the medical image or the region of interest included in the medical image into any of two or more classes. The classifier and the learner may be used together.

In addition, without providing the display control unit 46, the medical image processing apparatus 14 may output a composite image for display to the endoscope processor apparatus 12, and a display control unit (not illustrated) included in the endoscope processor apparatus 12 may cause the display apparatus 13 to display the composite image for display.

Although the endoscope processor apparatus 12 and the medical image processing apparatus 14 are different apparatuses in the above embodiments, the endoscope processor apparatus 12 and the medical image processing apparatus 14 may also be constituted as an integrated apparatus. That is, the functions of the medical image processing apparatus 14 may be provided in the endoscope processor apparatus 12.

In addition, the composite image generating unit 44 generates the second composite image, which is a composite of the medical image and the second notification information for storage, in the above embodiment, but, without limitation to this, may store the medical image and the second notification information in association with each other. In this case, the second notification information may be, for example, text information instead of image information indicating the second notification information, and may be added to the medical image as additional information. By making the second notification information text information, the second notification information can be edited. In addition, if the medical image is a moving image, a frame number of the moving image or a time stamp of a frame may be added to the second notification information corresponding to each frame so as to store the frame of the moving image and the second notification information in association with each other.

Furthermore, a hardware structure that performs various types of control of the medical image processing apparatus 14 according to the above embodiment is any of the following various processors. Various processors include a CPU (Central Processing Unit) that is a general-purpose processor functioning as various control units by executing software (programs), a programmable logic device (PLD) that is a processor in which the circuit configuration is changeable after manufacture, such as an FPGA (Field Programmable Gate Array), a dedicated electric circuit that is a processor having a circuit configuration that is specially designed to execute specific processing, such as an ASIC (Application Specific Integrated Circuit), and the like.

One processing unit may be constituted by one of these various processors, or may be constituted by two or more processors of the same type or different types (e.g., a combination of a plurality of FPGAs or a combination of a CPU and an FPGA). In addition, a plurality of control units may be configured as one processor. As a first example for configuring a plurality of control units as one processor, one or more CPUs and software may be combined to configure one processor, and this processor may function as a plurality of control units, as typified by a computer such as a client or a server. As a second example, a processor may be used that implements the functions of the entire system including a plurality of control units as one IC (Integrated Circuit) chip, as typified by a system on chip (SoC) or the like. In this manner, various processing units are constituted by one or more of the above various processors as a hardware structure.

In addition, the medical image as a processing target is time-series images or a still image captured by the endoscope 10 in the above embodiment, but, without limitation to this, may be a medical image captured by another modality such as an ultrasound diagnostic apparatus or an X-ray photography apparatus.

Furthermore, it is needless to say that the present invention is not limited to the above embodiments and that various modifications can be made without departing from the spirit of the present invention.

REFERENCE SIGNS LIST

9 endoscope system
10 endoscope
11 light source
12 endoscope processor apparatus
13 display apparatus
14 medical image processing apparatus
15 operating unit
16, 16A, 16B display
20 insertion part
21 handheld operating unit
22 universal cord
25 soft part
26 bending part
27 distal end part
28 imaging element
29 bending operation knobs
30 air/water supply button
31 suction button
32 still image capturing instruction unit
33 treatment tool introduction port
35 light guide
36 signal cable
37a connector
37b connector
38 moving image
38a frame images
39 still image
40 image acquiring unit
41 CPU
42 classification unit
42A input layer
42B intermediate layer
42C output layer
43 notification information generating unit
44 composite image generating unit
46 display control unit
47 memory
48, 48A, 48B storage
S10 to S22 step

What is claimed is:

1. A medical image processing apparatus comprising:
a processor configured to
acquire a medical image;
perform a classification of the medical image or a region of interest included in the medical image;
generate, in accordance with a classification result of the classification, first notification information for display and second notification information for storage, the second notification information differing from the first notification information; and
store the medical image and the second notification information on a storage, wherein the first notification information and the second notification information include the classification result, and wherein first information that indicates the classification result and is displayed based on the first notification information is different from second information that indicates the classification result and is displayed based on the second notification information.

2. The medical image processing apparatus according to claim 1, wherein the processor is further configured to store a composite image in which the medical image and the second notification information are composited on the storage.

3. The medical image processing apparatus according to claim 1, wherein the processor is further configured to store the medical image and the second notification information in association with each other on the storage.

4. The medical image processing apparatus according to claim 1, wherein the processor is further configured to generate a plurality of types of the second notification information, and store the plurality of types of second notification information in the storage.

5. The medical image processing apparatus according to claim 4, wherein the storage is constituted by a plurality of storages, wherein the processor is further configured to store each of the plurality of types of second notification information in each of the plurality of storages.

6. The medical image processing apparatus according to claim 1, wherein the processor is further configured to cause a display unit to display the medical image and the first notification information.

7. The medical image processing apparatus according to claim 6, wherein the display unit is constituted by a plurality of display units, wherein the processor is further configured to generate a plurality of types of the first notification information, and cause the plurality of display units to display the medical image and the plurality of types of the first notification information in a corresponding manner.

8. The medical image processing apparatus according to claim 1, wherein the processor is further configured to generate the first notification information in a notification form by which a patient does not understand details of the classification result and the second notification information indicating the details of the classification result.

9. The medical image processing apparatus according to claim 1, wherein the classification result includes information on a degree of reliability of a classified lesion, and wherein the processor is further configured to generate the first notification information in which the information on the degree of reliability is omitted and the second notification information including the information on the degree of reliability.

10. The medical image processing apparatus according to claim 1, wherein the processor is further configured to acquire a display region of the classification result on the basis of resolution information of a display unit and generate the first notification information in which details of the classification result are simplified in accordance with a size of the display region and the second notification information indicating the details of the classification result.

11. The medical image processing apparatus according to claim 1, wherein the processor is further configured to acquire time-series images as the medical image, and store the time-series images and the second notification information or stores a still image included in the time-series images and the second notification information on the storage.

12. The medical image processing apparatus according to claim 1, wherein the first information and the second information include at least one of text information, a symbol, and a degree of reliability.

13. A medical image processing method comprising:

acquiring a medical image;

performing a classification of the medical image or a region of interest included in the medical image;

generating, in accordance with a classification result of the classificationclassifying, first notification information for display and second notification information for storage, the second notification information differing from the first notification information;

causing a display unit to display the medical image and the first notification information; and storing the medical image and the second notification information on a storage, wherein the first notification information and the second notification information include the classification result, and wherein first information that indicates the classification result and is displayed based on the first notification information is different from second information that indicates the classification result and is displayed based on the second notification information.

14. The medical image processing method according to claim 13, wherein the first information and the second information include at least one of text information, a symbol, and a degree of reliability.

* * * * *